United States Patent
Vossough et al.

(10) Patent No.: US 11,254,559 B2
(45) Date of Patent: Feb. 22, 2022

(54) FET BASED SENSORY SYSTEMS

(71) Applicants: Kris Vossough, Palo Alto, CA (US); Farhang Yazdani, San Jose, CA (US)

(72) Inventors: Kris Vossough, Palo Alto, CA (US); Farhang Yazdani, San Jose, CA (US)

(*) Notice: Subject to any disclaimer, the term of this patent is extended or adjusted under 35 U.S.C. 154(b) by 115 days.

(21) Appl. No.: 15/911,133

(22) Filed: Mar. 4, 2018

(65) Prior Publication Data

US 2018/0186623 A1    Jul. 5, 2018

Related U.S. Application Data (60) Provisional application No. 62/467,222, filed on Mar. 5, 2017, provisional application No. 62/509,693, filed on May 22, 2017.

(51) Int. Cl.
*G01P 15/12* (2006.01)
*B81B 3/00* (2006.01)
(Continued)

(52) U.S. Cl.
CPC ............ *B81B 3/0021* (2013.01); *B82Y 15/00* (2013.01); *G01C 19/5712* (2013.01); *G01C 19/5783* (2013.01); *G01L 9/0042* (2013.01); *G01N 33/0027* (2013.01); *G01P 15/0802* (2013.01); *G01P 15/124* (2013.01); *H01L 29/0669* (2013.01); *H01L 29/84* (2013.01); *H04R 19/005* (2013.01); *H04R 19/04* (2013.01); *H04R 23/006* (2013.01); *B81B 2201/0214* (2013.01);
(Continued)

(58) Field of Classification Search
CPC .......... B81B 3/0021; B81B 2201/0214; B81B 2201/0242; B81B 2201/0235; B81B 2201/0257; B81B 2201/0264; B81B 2203/0118; B81B 2203/0127; G01P 15/0802; G01P 15/124; G01L 9/0042; G01N 33/0027; H01L 29/0669; H01L 29/84; H01L 29/16; H01L 29/1608; H01L 29/20; H01L 51/0048; H01L 29/775; H01L 29/0673; H04R 19/04; H04R 19/005; H04R 23/006; H04R 2201/003; G01C 19/5712; G01C 19/5783; B82Y 15/00
USPC ..... 73/504.12, 652, 654, 774, 777, 862.381, 73/862.621, 862.625, 862.636–862.639, 73/862.68, 717, 723, 504.04, 514.01, 73/514.02, 514.16, 514.35, 514.36
See application file for complete search history.

(56) References Cited

U.S. PATENT DOCUMENTS

3,356,915 A * 12/1967 Pomerantz ............... H03H 7/24
                                                                        257/417
4,812,888 A *  3/1989 Blackburn ............ G01L 9/0073
                                                                        257/254
(Continued)

*Primary Examiner* — Robert R Raevis
(74) *Attorney, Agent, or Firm* — Aslan Law, P.C.

(57) ABSTRACT

This invention describes the structure and function of an integrated multi-sensing system. Integrated systems described herein may be configured to form a microphone, pressure sensor, gas sensor, multi-axis gyroscope or accelerometer. The sensor uses a variety of different Field Effect Transistor technologies (horizontal, vertical, Si nanowire, CNT, SiC and III-V semiconductors) in conjunction with MEMS based structures such as cantilevers, membranes and proof masses integrated into silicon substrates. It also describes a configurable method for tuning the integrated system to specific resonance frequency using electronic design.

9 Claims, 11 Drawing Sheets

(51) Int. Cl.
*G01P 15/08* (2006.01)
*G01L 9/00* (2006.01)
*G01N 33/00* (2006.01)
*H01L 29/06* (2006.01)
*H01L 29/84* (2006.01)
*H04R 19/04* (2006.01)
*H04R 19/00* (2006.01)
*G01C 19/5712* (2012.01)
*H04R 23/00* (2006.01)
*G01C 19/5783* (2012.01)
*B82Y 15/00* (2011.01)
*H01L 29/16* (2006.01)
*H01L 29/20* (2006.01)
*H01L 51/00* (2006.01)
*H01L 29/775* (2006.01)

(52) U.S. Cl.
CPC ........... *B81B 2201/0235* (2013.01); *B81B 2201/0242* (2013.01); *B81B 2201/0257* (2013.01); *B81B 2201/0264* (2013.01); *B81B 2203/0118* (2013.01); *B81B 2203/0127* (2013.01); *H01L 29/0673* (2013.01); *H01L 29/16* (2013.01); *H01L 29/1608* (2013.01); *H01L 29/20* (2013.01); *H01L 29/775* (2013.01); *H01L 51/0048* (2013.01); *H04R 2201/003* (2013.01)

(56) References Cited

U.S. PATENT DOCUMENTS

| | | | | |
|---|---|---|---|---|
| 5,103,279 | A | * | 4/1992 | Gutteridge ............ G01P 15/124 257/254 |
| 5,457,368 | A | * | 10/1995 | Jacobsen ................ G01B 7/003 200/11 R |
| 5,500,549 | A | * | 3/1996 | Takeuchi ............ G01C 19/5719 257/415 |
| 2005/0135224 | A1 | * | 6/2005 | Mejia ....................... G01D 5/18 369/126 |
| 2014/0374804 | A1 | * | 12/2014 | Feyh ................... G01P 15/0802 257/254 |
| 2016/0274698 | A1 | * | 9/2016 | Ito ............................ G06F 3/044 |

\* cited by examiner

FET BASED SENSORY SYSTEMS

CROSS REFERENCE TO RELATED APPLICATIONS

This application claims the benefit of priority under 35 U.S.C. § 119(e) of U.S. provisional application Ser. No. 62/467,222, entitled "Vertical FET MEMS Microphone", filed Mar. 5, 2017 the content of which is incorporated herein by reference in its entirety.

The present application claims the benefit of priority to and is a continuation in part of U.S. patent application Ser. No. 62/509,693 entitled "Moving gate FET Sensors", filed May 22, 2017, the content of which is incorporated herein by reference in its entirety.

FIELD OF THE INVENTION

The subject matter herein relates to MEMS sensing and Field Effect Transistor (FET) of the semiconductor MEMS devices.

BACKGROUND OF THE INVENTION

Micro-Electro-Mechanical-Systems (MEMS) sensors are becoming increasingly popular as more sensors are being integrated in a variety of systems ranging from consumer electronics to automobile, aerospace, structural monitoring and life science applications. Although, the majority of the MEMS devices are still in the research and development phase, there is also the mature end of the industry that has been producing large volumes of pressure sensors, microphones, inertial motion sensors and gas sensors. The market for the mature MEMS devices has also been experiencing rapid growth as more applications are being developed with new and innovative packaging designs. Furthermore, new MEMS designs are constantly improving the device performance and integrate more functionality within the same chip, or package with smaller form factor. This has been an enabling factor for MEMS researchers to identify fundamental sensing mechanism and implement them, along with required circuitry, onto silicon chips.

New advances in the field of MEMS have broadened considerably the applications of these devices. MEMS technology has also enabled the miniaturization of the devices; a typical MEMS sensor is at least one order of magnitude smaller compared to a conventional sensor that is used to measure the same parameter. Consequently, MEMS devices can be batch-fabricated, this offers a high potential for unit cost reduction. Moreover, proper design can solve some problems related to power consumption, while providing improved performance characteristics, such as accuracy, sensitivity and resolution.

The current and the traditional MEMS sensor products consist of a sensing mechanical structure, i.e. a cantilever, or a membrane, that deflects upon sensing an external force, i.e. pressure, acoustic waves, or accelerations. The mechanical movement, such as deflection, is then converted into an electric signal through the use of piezo-resistive/electric material, or through changing capacitance between the moving part and a reference plate. There are also various geometries used to enhance the sensitivity and displacement range of these designs that would translate into better sensitivity and dynamic range of the overall sensor.

Microsensors and microactuators in MEMS have used a variety of transduction mechanisms. Each transduction mechanism has its own advantages that make it attractive for a given application and requirements such as low-cost, large-volume, high sensitivity, broad response range or superior noise performance. Some of the transduction mechanisms involve mechanical motion. Usually mechanical motion is converted to an electrical signal by measuring changes in passive elements such as capacitance, resistance, or mutual inductive coupling. In this embodiment a different sensing and actuation approach is pursued that directly couples mechanical motion with an active electrical device—a movable gate metal-oxide-semiconductor field effect transistor (MOSFET).

MEMS capacitive microphones are the most widely used microphones primarily for their low noise levels and high sensitivity. However, their sensitivity reduces with reducing size because of the decreasing air gap capacitance. The FET (filed effect transistor) microphone transduction, on the other hand, offers high sensitivity even with a smaller air gap capacitance, as the result of the miniaturization of the transducer. Multiple FET based MEMS structures are disclosed herein that maintain high sensitivity performance while employing integrated FET devices for transduction of the acoustic signal to electric current.

The moving gate transistor structure whose gate motion is along a lateral direction parallel to the substrate containing the channel has been investigated in the past. In these devices, movable gate transistor structure kept the channel width and the thickness of dielectric material constant. The gate overlap over the source or the drain changes as the gate moves. When the gate moves completely away from either the source or the drain end, the device operates in the subthreshold mode even when the gate voltage is above the threshold value. As the gate moves to overlap both the source and the drain edges, normal device current flows. This structure is, hence, sensitive to very small motion near the gate-source or gate-drain overlap regions. The device responds to small lateral gate motion typically less than 1 µm.

Similar type devices have also been used in BioTech for single molecule detection in solution. These FET devices detect characteristics of the surface charge structure of any macromolecule passing through a nanopore with vertical FET device implemented on the sidewalls. The vertical FET design directly amplifies the biomolecule's signal by several orders of magnitude with low noise. The sensor allows for the detection of a single charge at large distances, many times the diameter of the target molecule. As the result, this level of sensitivity can be exploited for acoustic vibration sensing in a lateral moving gate FET sensor.

Although some MEMS microphones have already been developed, size limitations requiring microphones to be small which lead to challenges in terms of frequency response and sensitivity. Capacitive microphones are usually composed of an elastic diaphragm and a perforated rigid back-plate, which constitutes a pair of sensing electrodes that behave like a variable capacitor. Deformation of the diaphragm due to variation in pressure leads to a corresponding change in the capacitance, $C_e$, and to an induced charge at the electrodes via the application of a direct-current (DC) polarization voltage across the electrodes. In an externally-polarized condenser microphone, the polarizing voltage is applied across a very large resistance, $R_e$. The variation in capacitance is measured from the change in the voltage across the resistor. The amplitude of this voltage signal will have a low-frequency cut-off determined from the time constant $1/R_e C_e$ due to the finite resistance. Therefore, further miniaturization of conventional microphones has led to a reduced size, which ultimately decreases the capacitance, $C_e$, which increases this cut-off frequency. This frequency limit can be overcome via careful preamp design or by replacing the DC bias voltage with a high-frequency AC bias voltage.

BRIEF SUMMARY OF THE INVENTION

This invention describes the structure and function of MEMS based vertical and horizontal moving gate Field Effect Transistor (FET) sensors. The sensing technology described herein may be configured to form wide range of MEMS sensors such as gyroscopes, accelerometers, microphones, pressure sensors, gas sensors, biosensors, and nanopores. The invention uses a moving gate structure over channel region of a vertically and horizontally integrated FET device.

DETAILED DESCRIPTION OF THE INVENTION

The various embodiments are described more fully with reference to the accompanying drawings. These example embodiments are provided so that this disclosure will be thorough and complete, and will fully convey the scope of the invention to readers of this specification having knowledge in the technical field. Like numbers refer to like elements throughout.

Figure 1:
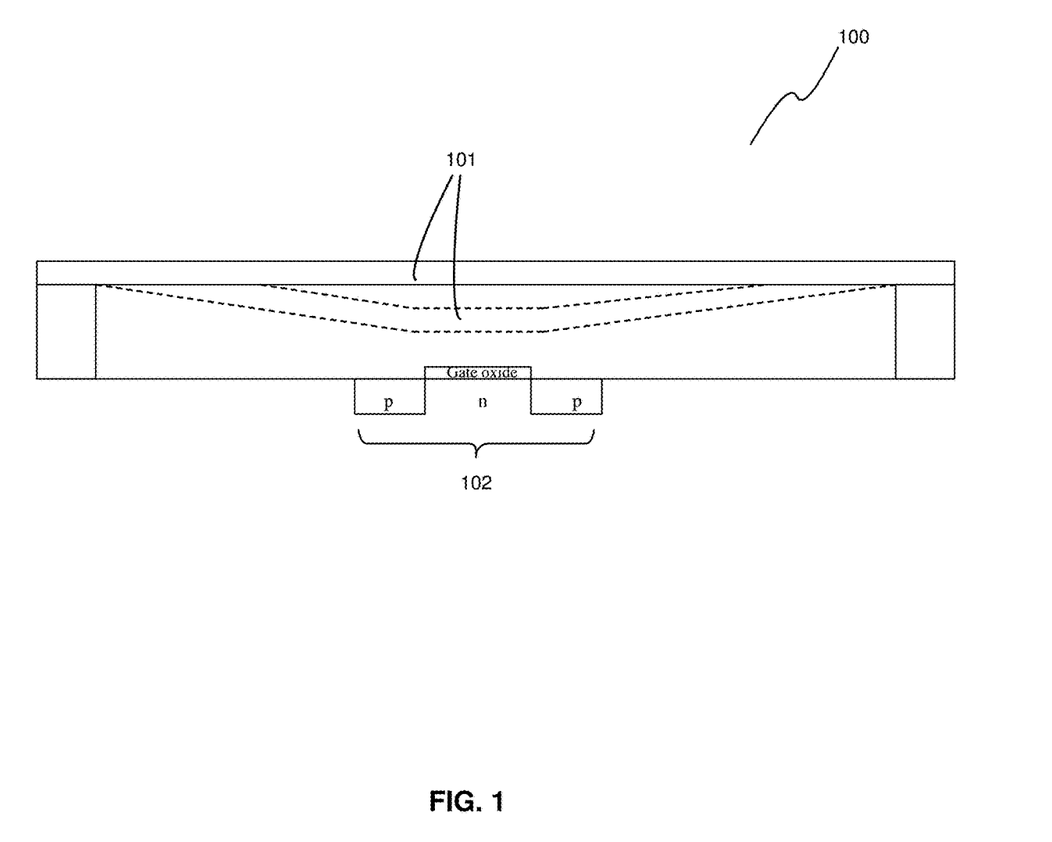
FIG. 1 is a side-view of a horizontal FET design for a MEMS microphone in accordance with an exemplary embodiment.
Figure 2:
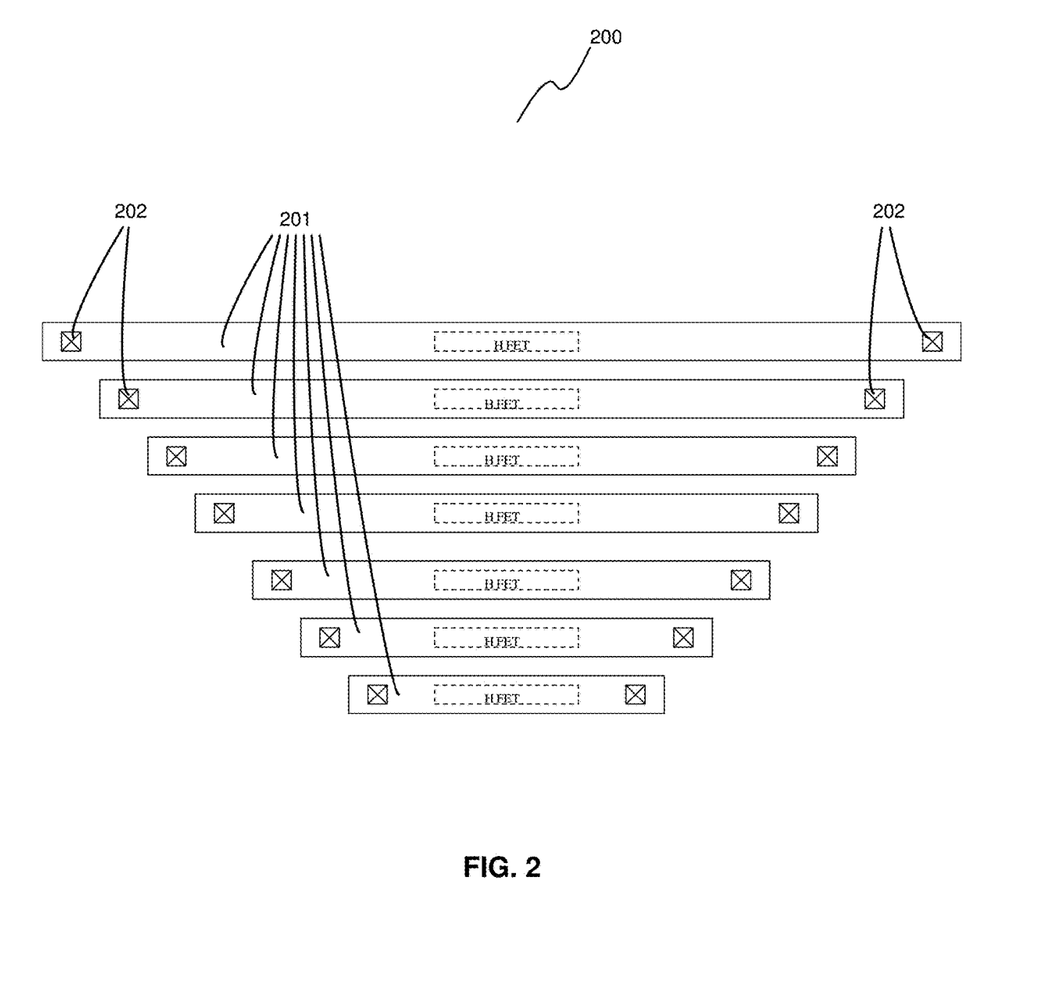
FIG. 2 is a top-view of horizontal FET design with variable suspended cantilevers for accurate acoustic signal measurement in accordance with an exemplary embodiment.

One exemplary embodiment of this invention involves a transduction mechanism that is based on changes in electric field in the separation between an electret and the channel-gate area of a field-effect transistor (FET), either directly, or indirectly through intermediary capacitors. An exemplary configuration is presented in FIG. 1, with the simplest structure 100 consisting of a flexible diaphragm 101 or cantilever 101 that works as the moving gate of the transistor 102. In another exemplary embodiment (FIG. 2) 200, the suspended cantilever design can be implemented with an array of different length cantilevers 201 to maximize response and sensitivity to various acoustic wavelengths. Cantilevers of various lengths 201 may be arranged in sequence as illustrated in FIG. 2 to increase sensitivity to a particular range of acoustic frequencies where each cantilever is anchored on both sides 202. This platform can also be used for differential and absolute pressure sensing. Similar sensing functionality can be integrated vertically into silicon with similar or higher sensitivity for sensing applications. It is understood that the exemplary embodiments presented can of any material or geometric design and used in any application or market. In all embodiments disclosed, air gaps maybe replaced by vacuum gaps to eliminate any damping effect due to presence of any fluid.

Figure 3:
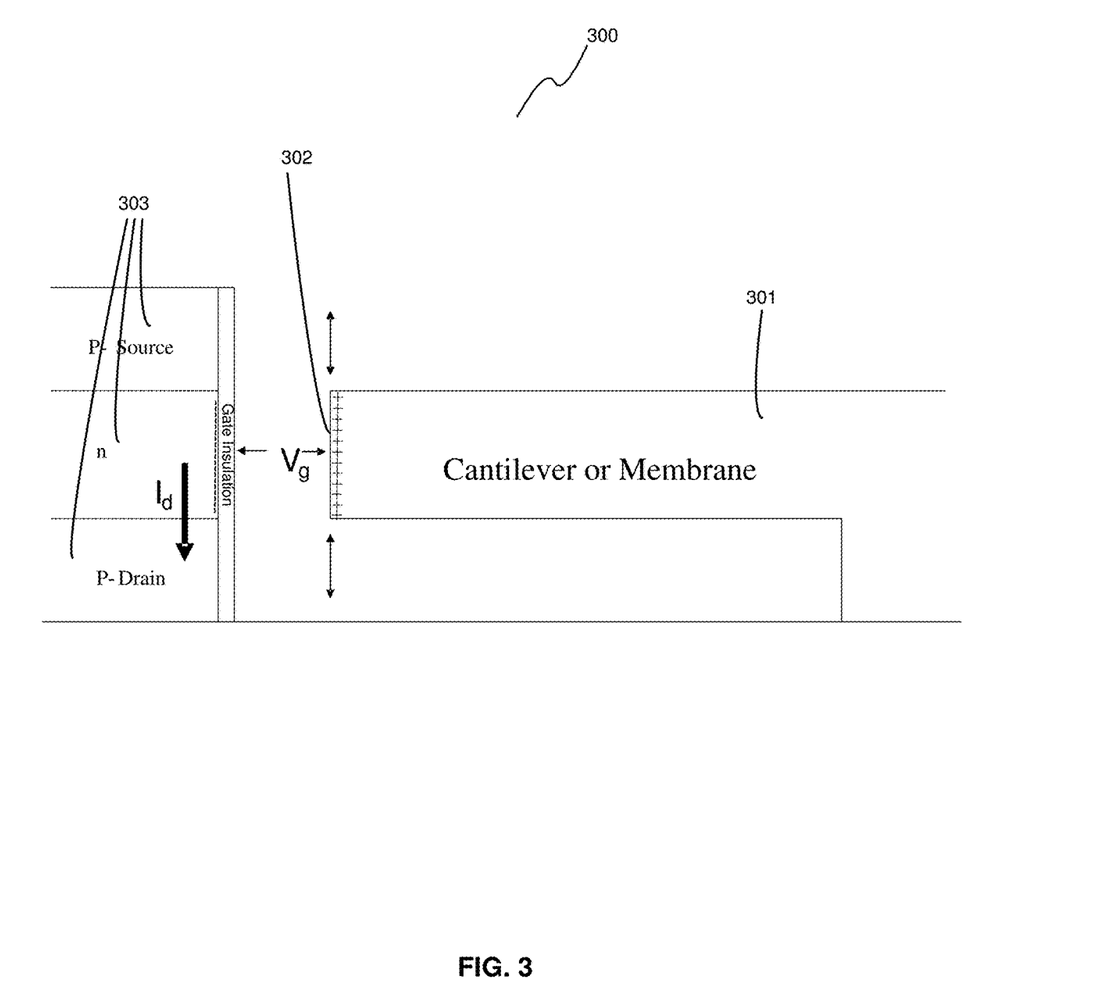
FIG. 3 is a side-view of a vertical FET design with variable suspended cantilevers for accurate acoustic signal measurement in accordance with an exemplary embodiment.

In another exemplary embodiment of this invention a vertically integrated FET with laterally moving gate is used to construct various sensors (FIG. 3). Vertical FET with laterally moving gate 300 comprises of a flexible cantilever 301 or a membrane 301 that behaves as the moving gate 302 of the transistor 303. The FET based integrated electromechanical transducer 300 can be made more sensitive to external acoustic pressure either by increasing the mechanical or the electrical sensitivities. The sensitivity of the transistor in general, determines the overall sensitivity of the structure. The proposed FET sensor 300 uses the transistor biased in the sub-threshold region (or any other appropriate transistor mode) where the drain current depends exponentially on the difference between the gate-to-source voltage and the threshold voltage. The sensitivity of the sensor 300 can also be improved without adding any complexity in the mechanical design of the cantilever/membrane 301.

In this exemplary embodiment (FIG. 3), sensor 300 comprises of an elastic cantilever/membrane 301 which deflects due to the incident sound pressure. This deflection causes the cantilever/membrane 301 to move in parallel with the channel length of the transistor 301, thereby, changing the overlap between the moving gate 302 over the channel region of the transistor 301. The edge of the cantilever (or membrane) will act as a moving gate of the adjacent p-wells and will induce a conduction channel between the p-wells on the sidewall. Variable electric field applied to the cantilever edge will affect the formation of a charge channel, across the overlap in the gate region of the FET. The change in the overlap changes the drain current ($I_d$) which determines the sensor response. For a constant gate source voltage ($V_{gs}$) less than threshold voltage ($V_t$), ($V_{gs} < V_t$) when the overlap changes, the $V_t$ changes and this leads to a change in drain current ($I_d$). The back gate voltage is assumed zero and the source is assumed to be grounded as well. For example, any acoustic or pressure induced movement of the cantilever will change the conductivity of the channel and, therefore, the source to drain current within the FET device. The subsequent change in the source-to-drain current can then correlate to the magnitude of the acoustic or pressure signal sensed by the cantilever. This configuration provides various mechanical and electronic parameters for tuning and increased sensitivity of the sensing, or any other sensing parameter.

The vertical FET sensing using a laterally moving gate has shown greater sensitivity than the horizontal FET with vertical moving gate. The lateral moving gate design can be used as a sensing platform for a variety of different MEMS sensors with high sensitivities. In comparison to the vertically moving gate FET structure, the laterally moving gate provides a number of different transistor operation parameters (i.e. transistor operation modes and bias voltages, etc.) for the user to tune the FET structure electronically, in order to detect the desired signals in the form of vibration across the gate region. Furthermore, transistor gate width, length, location and geometry can be designed to maximize sensitivity and dynamic range of the sensing devices. There are many parameters available to design various sensors with great sensitivity by choosing the right junction depths for the P-wells and operating the transistor in different modes with different biases to achieve maximum sensitivity and dynamic range. This sensing platform (FIG. 3) is applicable to a variety of different MEMS sensors such MEMS microphone (acoustics), pressure sensing, accelerometers, gyroscopes and combined Inertial Measurement Units (IMU).

In an exemplary embodiment of this invention (FIG. 3) the vertical FET with laterally moving gate can also function as a vertical FET with vertically moving gate (not shown). In vertical FET with laterally moving gate, the gate moves in parallel to the gate channel, whereas, in the vertical FET with vertically moving gate, the gate movement is perpendicular direction to the FET channel. In this configuration the gate has 2 Degrees of Freedom (DOF) movement in relation to the FET channel, parallel and perpendicular. This is a necessary requirement for sensing Coriolis force on a proof mass which is the foundation of construction of gyroscopes. In addition, parallel and perpendicular moving gates can also be incorporated into a horizontal FET device.

Figure 4:
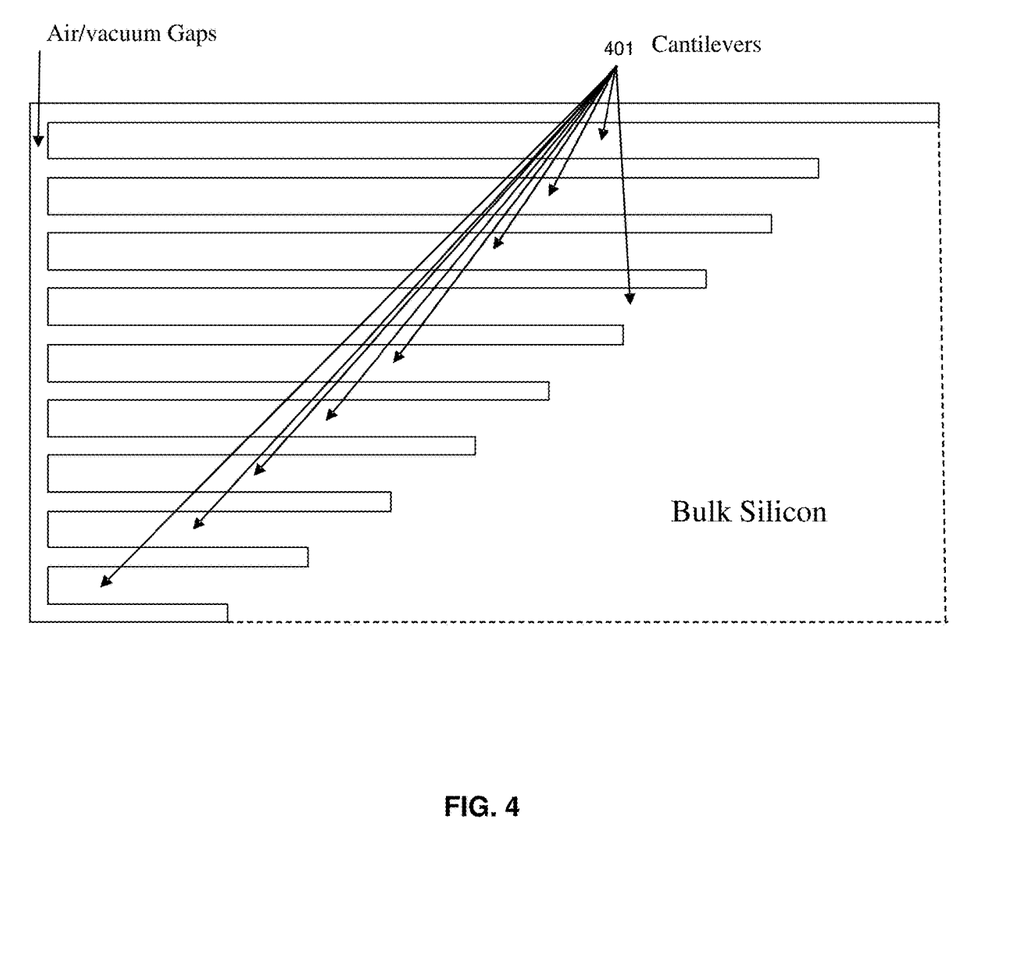
FIG. 4 is a top view of vertical FET design with variable suspended cantilevers for accurate acoustic signal measurement in accordance with an exemplary embodiment.

In another exemplary embodiment of this invention (FIG. 4), the vertical FET with laterally moving gate (not shown) can be integrated with cantilevers of varying size 401, and geometry for a variety of acoustic, vibration and acceleration sensing. In acoustic sensing, the cantilevers lengths of varying sizes can be used within the same device in order to optimize the frequency response time of the device to a range of frequencies and signal strengths. In sensing acceleration and inertial moment, a proof mass of various sizes and geometries, can be integrated at free end of each cantilever to detect signals with the appropriate frequency and sensitivity.

Figure 5:
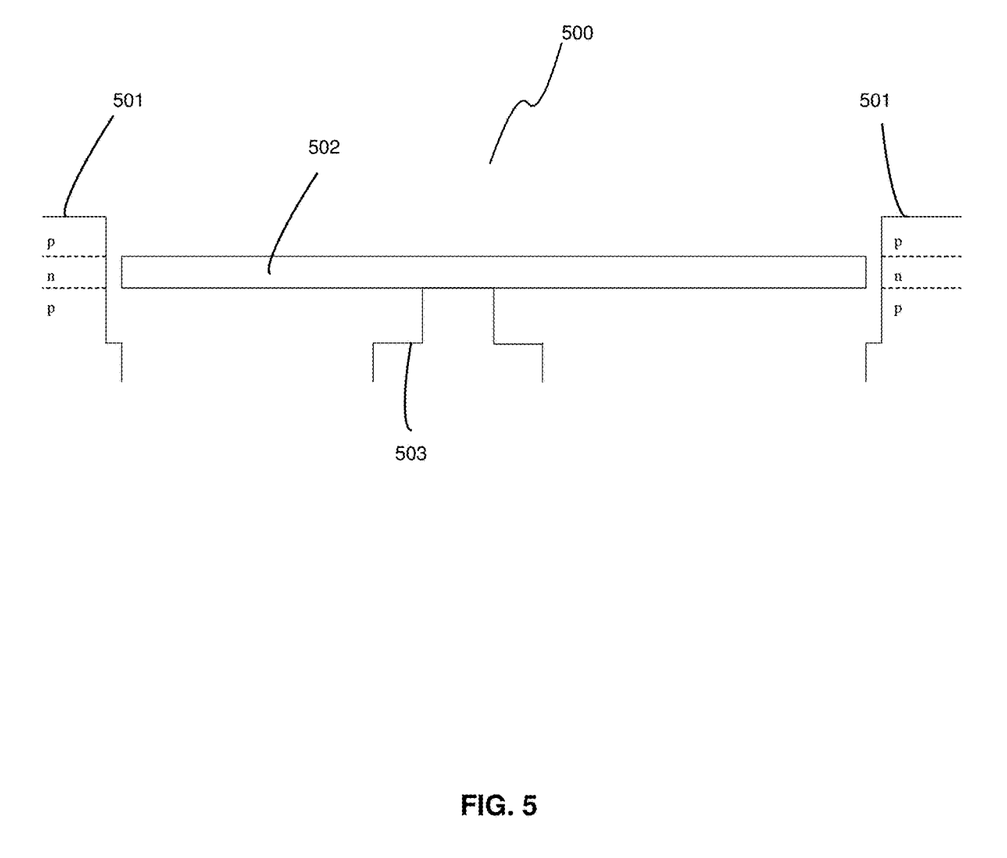
FIG. 5 is a side view of vertical FET microphone design with pedestal supported membrane for accurate acoustic signal measurement in accordance with an exemplary embodiment.

In another exemplary embodiment of this invention (FIG. 5) the vertical FET with laterally moving gate microphone is demonstrated. Sensor 500 eliminates the two main limitations of the latest state of the art high performance and the traditional electret microphones resulting from the backplate and the bound membrane structures. The primary factor in high noise level of the current commercial microphones has been the existence of the backplates in high performance capacitive microphones. The thermal noise and the damping effect of the microphones available in the market are due to the existence of the backplate structure, whereas this invention 500 eliminates the need for a backplate. This invention 500 uses an unbound membrane 502 on a pedestal 503 without the backplate to overcome these limitations. Vertical FET 501 with laterally moving gate unbound membrane 502 is used to sense the acoustic signals captured by the membrane 502. The noise level in this invention 500 is expected to be significantly lower than the current high performance MEMS microphones while the dynamic range is expected to be higher as the result of the unbound membrane 502. Another benefit of the unbound membrane structure 502 is a significantly lower signal distortion which exists in traditional bound membrane microphones.

Figure 6:
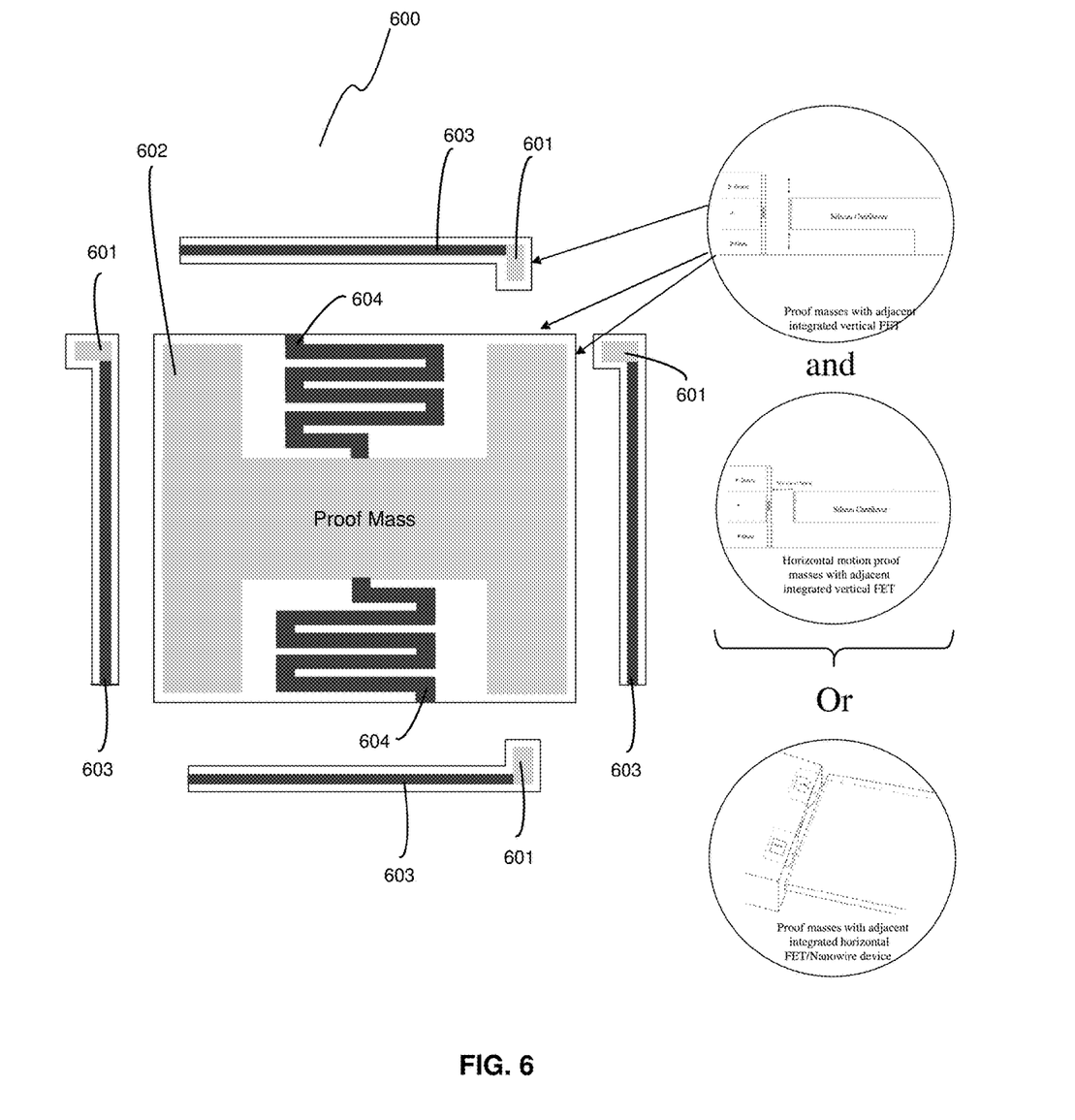
FIG. 6 is a top view of 6 Degrees of Freedom (DOF) MEMS Inertial Measurement Unit (IMU) gyroscope, based on vertical or horizontal or nanowire FET platform in accordance with an exemplary embodiment.

Any accelerometer, gyroscope or in general IMUs will require the implementation of a proof mass at the end of each cantilever or membrane with multiple axis of freedom. In another exemplary embodiment of this invention (FIG. 6) proof masses of various sizes and shapes 601, 602 can be placed at the free end of each cantilever 603, 604 or membrane (not shown). Furthermore, any gyroscope applications will require an additional degree of freedom sensing for each proof mass (every proof mass has to have freedom of movement in, at least, two directions). In this exemplary embodiment, two DOF moving gates can be accomplished by a laterally moving gate and a vertically moving gate away from the channel region. In FIG. 6 only two examples of proof masses 601, 602 mounted on cantilevers are shown that can measure the Coriolis force. This enables every proof mass at the end of a cantilever to be able to move freely (vibrate) in vertical (out of plane) and sideways (in-plane) directions. Simultaneously, the vibration displacement in both directions can be measured by the vertical FET sensor(s) placed around the proof mass. This embodiment takes advantage of simultaneous displacement measurement along (at least) two axis for IMU/accelerometer designs. It should be noted that the proof mass resonates in one direction and displaces in another direction, perpendicular to resonant displacement direction, due to Coriolis force. The proof mass on a cantilever structure 603 with 2 degrees of freedom movements constitute a simple 2-axis accelerometer. A similar structure orthogonal to the first structure can measure acceleration along the $3^{rd}$ axis.

Multiple different designs can be achieved by placing FET sensors around any suspended proof mass configuration which makes designs for a gyroscope/accelerometer combination possible. As an example, a simple 6-axis gyroscope/accelerator design with a central proof mass can be implemented as shown in FIG. 6. The central proof mass structure 602 has multiple (3 DOF) movement for sensing the Coriolis forces resulting from angular rotation along all 3-axis. Displacement measurement along all 3-axis is also possible with alternative designs of proof mass 602. It is understood that many design configuration of proof masses 601, 602 and cantilevers 603, 604 are possible for 6 axis of freedom IMUs. The central proof mass configuration 602 is just one example of a simultaneous 3 DOF movement and measurement which constitutes 6 DOF IMU.

Another embodiment of the moving gate FET sensor may be incorporated into a multi-axis gyroscope/accelerometer (not shown). The 6-axis gyroscope may be constructed with either the vertical, or the horizontal FET configuration. It is understood that this FET configuration can be realized using various technologies including, silicon nanowire, carbon nanotube, silicon carbides and III-V semiconductors just to name a few.

Figure 7:
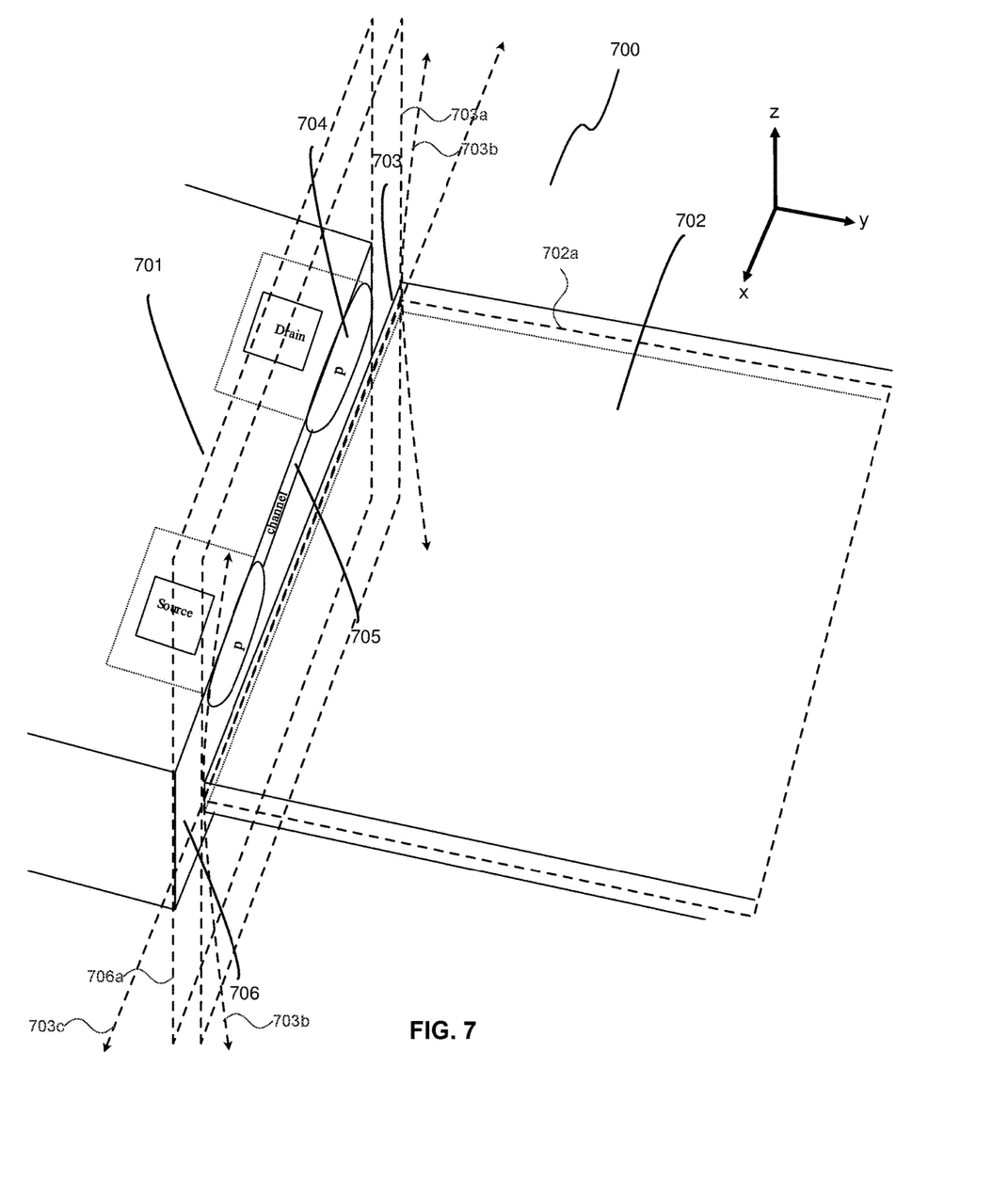
FIG. 7 is the 3D view of a horizontal FET design with a supported cantilever (or membrane) for accurate acoustic signal measurement in accordance with an exemplary embodiment.

Another embodiment of this invention (FIG. 7) discloses a horizontal FET 701 with moving gate built into a separate structure facing the suspended cantilever 702, or unbound membrane 702 absorbing the acoustic signals. Note the three-dimensional coordinate system in the figure showing x, y, and z axes. In FIG. 7, sidewall 706 has a face that generally defines a plane (a "face plane 706a," of the sidewall, that extends in the x- and the z-directions). The cantilever (or membrane) 702 has an edge 703. The edge 703 is a face that, in the position illustrated, generally defines a plane (an "edge plane 703a," of the edge 703, that extends in the x- and z-directions). The cantilever (or membrane) has a width in the x- direction, a length in the y-direction, and a thickness in the z-direction. The cantilever (or membrane), when in the illustrated position, generally defines a plane (a "center plane 702a," of the cantilever or membrane, that extends in the x- and y-directions). The center plane 702a is normal to the face plane 706a and the edge plane 703a, and passes through the center of the thickness of the cantilever (or membrane). Line 703c illustrates a line along the middle of the edge 703 of the cantilever (or membrane). Line 703c extends along the x-direction. The edge of the cantilever (or membrane) 703 will act as a moving gate of the adjacent p-wells 704 and will induce a conduction channel 705 between the p-wells 704 on the sidewall 706, by applying a bias voltage to the cantilever (membrane) 702. The subsequent movement of the cantilever edge across the channel area is shown by dashed lines that illustrate a somewhat arcuate path 703b which is a path that is curved about a radius of curvature. Movement of the edge 703 along the somewhat arcuate path 703b occurs when the cantilever (or membrane) 702 is fixed at some point along its length (not shown in FIG. 7, but note for example FIG. 3 where the cantilever or membrane 301 extends from a fixed point). The movement of the edge 703 across the channel area will effect a change in the drain current, $I_d$, of the FET that corresponds to the displacement of the cantilever with respect to the FET channel. There are many parameters available to the designer to design an acoustic sensor with great sensitivity by choosing the right junction depths for the P-wells and operating the transistor in different modes with different biases to achieve maximum sensitivity and dynamic range.

The moving gate 703 will be in the proximity of the sidewall 706 of the horizontal FET device such that the electric field from the gate will create a channel 705 between the p-wells 704 on the sidewall 706. The depth of the p-well 704 junctions can be determined by the amount of deflection of the cantilever/diaphragm edge 703. Deflections of the cantilever/diaphragm edge 703 below the p-well 704 junction depths will result in sub-threshold state of the FET with sufficient sensitivity to register very weak acoustic signals. In effect, the trans-conduction converts mechanical displacement to a sub-threshold transistor with a modulating channel 705 length. Other modes of transistor operations (i.e. inversion mode) are also suitable in producing highly sensitive drain current output.

Similarly, the cantilever edge 703 may move in the direction perpendicular to the sidewall 706, or vertically away from the channel region of the FET (not shown) in order to produce similar change in the drain current, $I_d$, of the FET that will correspond to the vertical displacement of the cantilever edge 703 from the channel 705. The junction depths and doping levels of the horizontal FET may be optimized in order to provide maximum sensitivity for a range of displacements, both laterally (horizontal to sidewall channel) and vertically (perpendicular to sidewall channel) across the FET channel.

Figure 8:
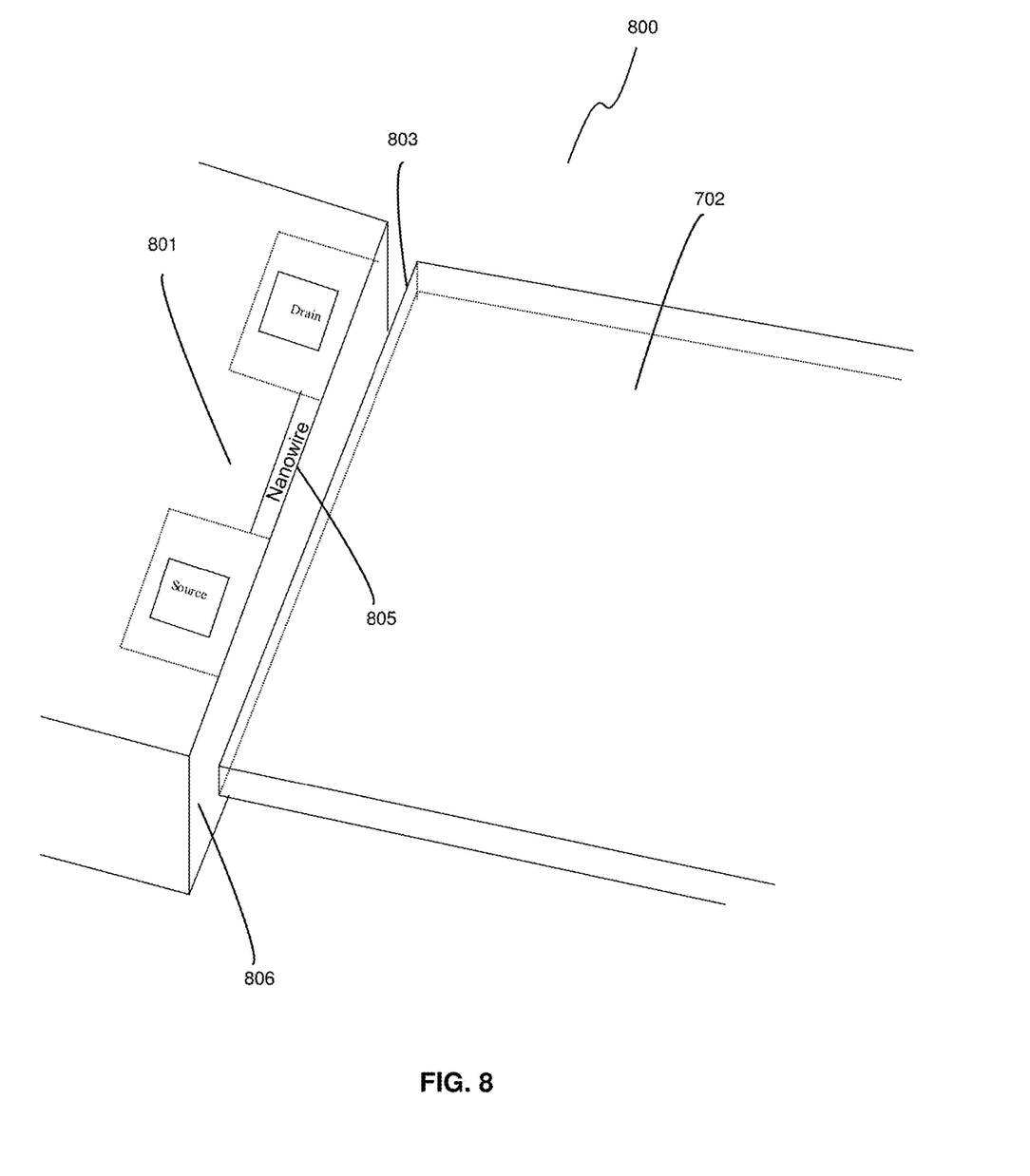
FIG. 8 is the 3D view of a horizontal nanowire FET design with a supported cantilever (or membrane) for accurate acoustic signal measurement in accordance with an exemplary embodiment.

In another exemplary embodiment of this invention 800 (FIG. 8), a horizontal integrated FET 801, as described earlier, may also be implemented using a variety of available technologies, including silicon nanowires, carbon nanotubes (CNT), silicon carbide (SiC), type III-V semiconductors, and more. A horizontal FET 801 design with silicon nanowire or CNT can be implemented by precise positioning of the FET nanowire 805 on the edge of the sidewall 806, as shown in the FIG. 8. The sensing mechanism is the same as before, but the $I_d$ characteristics of the nanowire (and CNT) is much more sensitive to small changes in the gate voltage which corresponds to cantilever displacement. The drain current vs. gate voltage in an active nanowire transistor have an exponential relation. This offers a high degree of sensitivity, and resolution, for the overall sensor that will surpass the silicon FET performance. Furthermore, a vertical integrated FET can also be realized with similar technologies (i.e. SiC, III-V semiconductors, CNT and silicon nanowires) and similar sensing sensitivities.

Figure 9:
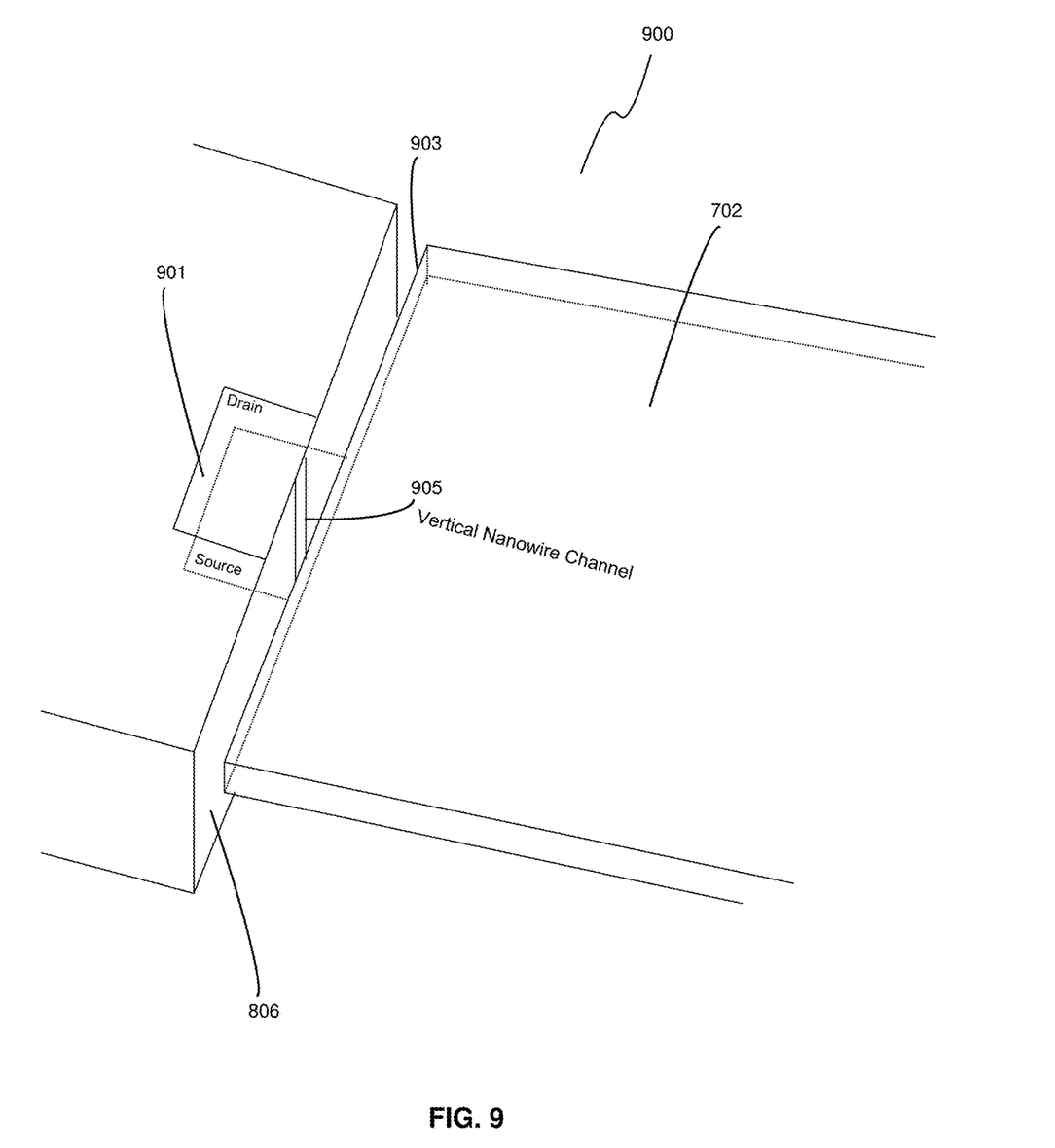
FIG. 9 is the 3D view of a vertical nanowire FET design with a supported cantilever (or membrane) for accurate acoustic signal measurement in accordance with an exemplary embodiment.

In another exemplary embodiment of this invention 900 (FIG. 9), A vertical nanowire FET 901 is constructed with a nanowire 905, it is understood that other technologies such as SiC, type III-V semiconductors and carbon nanotube transistor which exhibits higher drain current sensitivity can be employed. The vertical nanowire transistor 901 will operate similar to the horizontal FET by modulating the channel length 905, whereas, the horizontal nanowire transistor will sense the voltage gap between the channel-gate region and the vibrating edge 903 of cantilever/membrane 702.

Figure 10A:
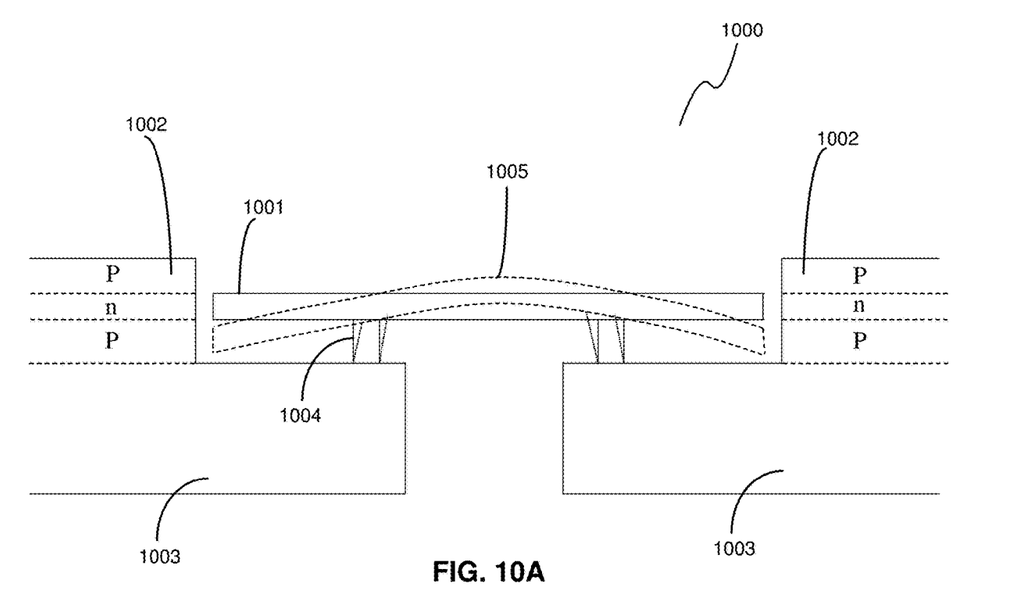
FIG. 10A is the side view of a vertical FET design membrane for accurate pressure sensing in accordance with an exemplary embodiment.

In another exemplary embodiment of this invention 1000 (FIG. 10A) an integrated vertical FETs are disclosed. A practical and efficient means of fabrication for the vertical FET devices is critical, this embodiment provides simplified approach to fabrication. A circular membrane 1001 is surrounded by one or more vertical FET(s) 1002 as depicted in FIG. 10A, the circular membrane 1001 is connected to substrate 1003 using elevated circular post (membrane support structure) 1004 in such a way that the circular membrane 1001 can deflect 1005 and sense a differential pressure.

Figure 10B:
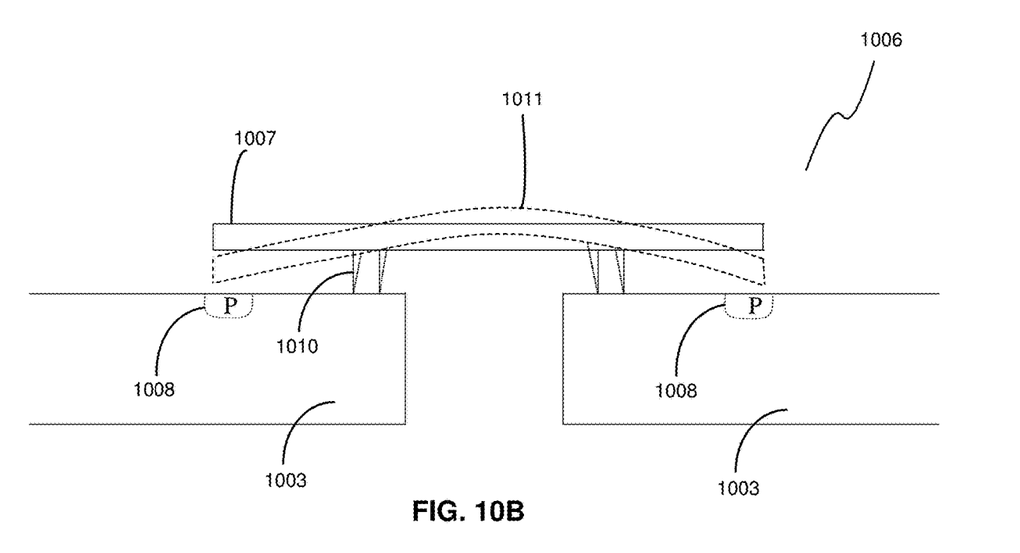
FIG. 10B is the side view of a horizontal FET design membrane for accurate pressure sensing in accordance with an exemplary embodiment.

In another exemplary embodiment of this invention 1006 (FIG. 10B) an integrated horizontal FETs are disclosed. A practical and efficient means of fabrication for the horizontal FET devices is critical, this embodiment provides simplified approach to fabrication. A circular (or any other shape) membrane 1007 is surrounded by one or more vertical FET(s) 1008 as depicted in FIG. 10B, the circular membrane 1008 is connected to substrate 1003 using elevated circular post (membrane support structure) 1010 in such a way that the circular membrane 1008 can deflect 1011 and sense a differential pressure.

The key advantage of the embodiment disclosed herein 1000, 1006 is the simplicity of fabrication using an additive process technology. The circular post 1004, 1010 (membrane support structures) connecting the membrane to the substrate may also be constructed with piezoelectric materials for sensing pressure, or acoustic signals.

The single suspended membrane 1001, 1007 can be fabricated using a 3 mask additive semiconductor process. Both vertical and horizontal FET sensors can be integrated into this pressure sensing design that takes advantage of the enhanced deflection on the edge of the membrane. The size and properties of the circular posts 1004, 1010 (membrane support structures) connecting the membrane 1005, 1011 to the substrate 1003, 1009 is critical in determining overall sensitivity to acoustic signals and pressure changes. Since the maximum stress and strain during pressure change occurs in these support structures 1004, 1010, therefore, sensing elements such as piezoelectric thin films can be used for sensing pressure and acoustic signals, instead of FET devices 1002, 1008.

Figure 11A:
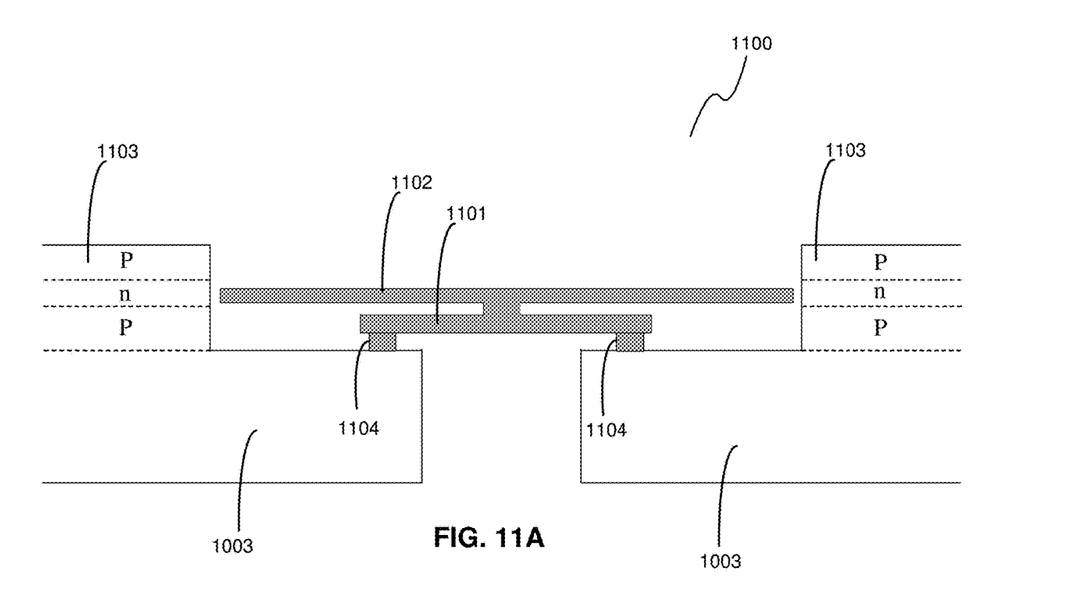
FIG. 11A is the side view of a vertical FET design with double membranes, or membrane/cantilever for accurate pressure sensing in accordance with an exemplary embodiment.

In another exemplary embodiment of this invention 1100 (FIG. 11A) a secondary unbound membrane 1102 is fabricated on top of the sensing membrane 1101 in such a way as to transfer maximum deflection of the sensing membrane 1101. The unbound secondary membrane would act as the laterally moving gate for the vertical FET sensor 1103. The circular sensing membrane 1101 is connected to substrate 1003 using elevated circular post (membrane support structure) 1104 in such a way that the circular membrane 1101 can deflect and sense a differential pressure.

Figure 11B:
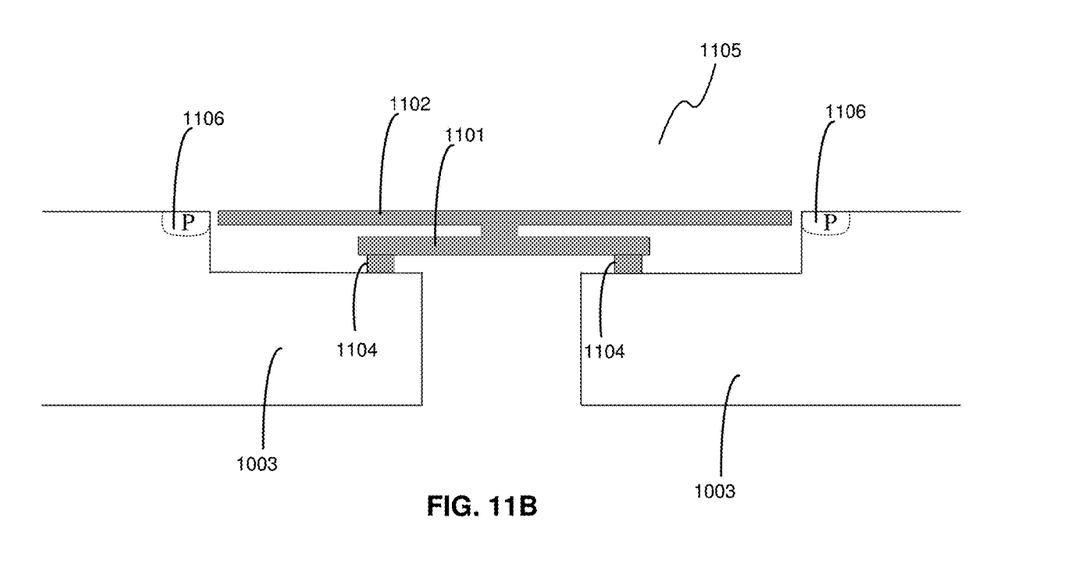
FIG. 11B is the side view of a horizontal FET design with double membranes, or membrane/cantilever for accurate pressure sensing in accordance with an exemplary embodiment.

In another exemplary embodiment of this invention 1105 (FIG. 11B) a secondary unbound membrane 1102 is fabricated on top of the sensing membrane 1101 in such a way as to transfer maximum deflection of the sensing membrane 1101. The unbound secondary membrane would act as the laterally moving gate for the horizontal FET sensor 1106. The circular sensing membrane 1101 is connected to substrate 1003 using elevated circular post (membrane support structure) 1104 in such a way that the circular membrane 1101 can deflect and sense a differential pressure. A proof mass may be placed on any of the membranes.

The exemplary suspended double membrane disclosure 1100, 1105 (FIG. 11A, 11B) can be fabricated using a 5 mask additive semiconductor process. Both vertical and horizontal FETs 1103, 1106 sensors can be integrated into a pressure, acoustic or gas sensing designs that takes advantage of registering maximum deflection of the bottom membrane. It is understood that the top membrane 1102 can also be designed in the form of any other shape or structure that can interact properly with the integrated FET devices.

Having disclosed several embodiments, it will be recognized by those of skill in the art that various modifications, alternative constructions, and equivalents may be used without departing from the spirit of the disclosed embodiments. Additionally, a number of well-known processes and elements have not been described to avoid unnecessarily obscuring the embodiments described herein. Accordingly, the above description should not be taken as limiting the scope of the claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the embodiments described, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the dielectric material" includes reference to one or more dielectric materials and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A sensor comprising:
   one or more transistor portions, wherein
   said one or more transistor portions include at least a source, a drain, and a channel, and are arranged by a sidewall that defines a face plane of the one or more transistor portions; and
   one or more sensing elements, wherein
   an edge of said one or more sensing elements behaves as moving gate of said one or more transistor portions,
   an electric field is applied to said edge of said one or more sensing elements,
   said one or more transistor portions is/are biased,
   said one or more sensing elements is/are flexible,
   source wells and drain wells of said one or more transistor portions can be coplanar or stacked,
   said edge of said one or more sensing elements moves along a path that is curved about a radius of curvature, wherein a line along a middle of said edge stays parallel to the face plane as said edge moves along the path,
   said edge of said one or more sensing elements is separated from said one or more transistor portions by a gap,
   there is no physical contact between said edge of said one or more sensing elements and said one or more transistor portions, and
   said one or more sensing elements is/are one or more membranes.

2. The sensor according to claim 1, wherein
   said one or more sensing elements can flex due to acoustic signals,
   said one or more sensing elements can flex due to pressure,
   said one or more sensing elements can flex due to inertial force, and
   deflection in said one or more sensing elements modulates a drain current in said one or more transistor portions.

3. The sensor according to claim 1, wherein
   said one or more sensing elements can flex due to acoustic signals,
   said one or more sensing elements can flex due to pressure,
   said one or more sensing elements can flex due to inertial force,
   deflection in said one or more sensing elements modulates a drain current in said one or more transistor portions, and
   the magnitude of the change in said drain current determines the sensitivity to said acoustic signals or said pressure or said inertial force.

4. A sensor comprising:
   one or more transistor portions, wherein
   said one or more transistor portions include at least a source, a drain, and a channel, and are arranged by a sidewall that defines a face plane of the one or more transistor portions; and
   one or more sensing elements, wherein
   an edge of said one or more sensing elements behaves as moving gate of said one or more transistor portions,
   an electric field is applied to said edge of said one or more sensing elements,
   said one or more transistor portions is/are biased,
   said one or more sensing elements is/are flexible, source wells and drain wells of said one or more transistor portions can be coplanar or stacked,
said edge of said one or more sensing elements moves along a path that is curved about a radius of curvature, wherein a line along a middle of said edge stays parallel to the face plane as said edge moves along the path,
said edge of said one or more sensing elements is separated from said one or more transistor portions by a gap,
there is no physical contact between said edge of said one or more sensing elements and said one or more transistor portions,
said one or more sensing elements is/are one or more membranes,
said one or more membranes can flex due to acoustic signals,
said one or more membranes can flex due to pressure,
said one or more sensing elements can flex due to inertial force, and
deflection in said one or more membranes modulates a drain current in said one or more transistor portions.

5. A sensor comprising:
one or more transistor portions, wherein
said one or more transistor portions include at least a source, a drain, a channel, and are arranged by a sidewall that defines a face plane of the one or more transistor portions; and
one or more sensing elements, wherein
an edge of said one or more sensing elements behaves as moving gate of said one or more transistor portions,
an electric field is applied to said edge of said one or more sensing elements,
said one or more transistor portions is/are biased,
said one or more sensing elements is/are flexible,
source wells and drain wells of said one or more transistor portions can be coplanar or stacked,
said edge of said one or more sensing elements moves along a path that is curved about a radius of curvature, wherein a line along a middle of said edge stays parallel to the face plane as said edge moves along the path,
said edge of said one or more sensing elements is separated from said one or more transistor portions by a gap,
there is no physical contact between said edge of said one or more sensing elements and said one or more transistor portions,
said one or more sensing elements is/are one or more membranes,
said one or more membranes can flex due to acoustic signals,
said one or more membranes can flex due to pressure,
said one or more sensing elements can flex due to inertial force,
deflection in said one or more membranes modulates a drain current in said one or more transistor portions, and
the magnitude of the change in said drain current determines the sensitivity to said acoustic signals or said pressure or said inertial force.

6. A sensor comprising:
one or more transistor portions, wherein
said one or more transistor portions include at least a source, a drain, and a channel, and are arranged by a sidewall that defines a face plane of the one or more transistor portions; and
one or more sensing elements, wherein
an edge of said one or more sensing elements behaves as moving gate of said one or more transistor portions,
an electric field is applied to said edge of said one or more sensing elements,
said one or more transistor portions is/are biased,
said one or more sensing elements is/are flexible,
source wells and drain wells of said one or more transistor portions can be coplanar or stacked,
said edge of said one or more sensing elements moves along a path that is curved about a radius of curvature, wherein a line along a middle of said edge stays parallel to the face plane as said edge moves along the path,
said edge of said one or more sensing elements is separated from said one or more transistor portions by a gap,
there is no physical contact between said edge of said one or more sensing elements and said one or more transistor portions,
said one or more sensing elements is/are one or more membranes,
said one or more membranes can flex due to acoustic signals,
said one or more membranes can flex due to pressure,
said one or more sensing elements can flex due to inertial force,
deflection in said one or more membranes modulates a drain current in said one or more transistor portions,
the magnitude of the change in said drain current determines the sensitivity to said acoustic signals or said pressure or said inertial force,
said one or more membranes is/are attached to a substrate using elevated membrane support structure, and
said one or more membranes is/are arranged in stacked configuration to transfer maximum deflection of a sensing membrane.

7. A sensor comprising:
one or more transistor portions, wherein
said one or more transistor portions include at least a source, a drain, and a channel, and are arranged by a sidewall that defines a face plane of the one or more transistor portions; and
one or more sensing elements, wherein
an edge of said one or more sensing elements behaves as moving gate of said one or more transistor portions,
an electric field is applied to said edge of said one or more sensing elements,
said one or more transistor portions is/are biased,
said one or more sensing elements is/are flexible,
source wells and drain wells of said one or more transistor portions can be coplanar or stacked,
said edge of said one or more sensing elements moves along a path that is curved about a radius of curvature, wherein a line along a middle of said edge stays parallel to the face plane as said edge moves along the path,
said edge of said one or more sensing elements is separated from said one or more transistor portions by a gap,
there is no physical contact between said edge of said one or more sensing elements and said one or more transistor portions,
said one or more sensing elements is/are attached to a substrate using elevated membrane support structure, and
said one or more sensing elements is/are arranged in stacked configuration to transfer maximum deflection of a sensing membrane.

8. A sensor comprising:
one or more transistor portions, wherein
said one or more transistor portions include at least a source, a drain, and a channel, and are arranged by a sidewall that defines a face plane of the one or more transistor portions; and
one or more sensing elements, wherein
an edge of said one or more sensing elements behaves as moving gate of said one or more transistor portions,
an electric field is applied to said edge of said one or more sensing elements,
said one or more transistor portions is/are biased,
source wells and drain wells of said one or more transistor portions can be coplanar or stacked,
said edge of said one or more sensing elements moves along a path that is curved about a radius of curvature, wherein a line along a middle of said edge stays parallel to the face plane as said edge moves along the path,
said edge of said one or more sensing elements is separated from said one or more transistor portions by a gap,
there is no physical contact between said edge of said one or more sensing elements and said one or more transistor portions, and
said one or more sensing elements is/are one or more membranes.
9. The sensor according to claim 8, wherein
said one or more sensing elements is/are flexible.

* * * * *